(12) United States Patent
Cannady et al.

(10) Patent No.: US 8,821,808 B2
(45) Date of Patent: Sep. 2, 2014

(54) STERILIZATION WRAPS AND METHODS FOR STERILIZING ARTICLES

(71) Applicant: Allegiance Corporation, McGaw Park, IL (US)

(72) Inventors: Clay Cannady, Highland Park, IL (US); Michael Duski, Buffalo Grove, IL (US); Brian G. Hoge, Fletcher, NC (US); Gregory Stecklein, Lake Villa, IL (US); James F. Whitaker, Alexander, NC (US)

(73) Assignee: Allegiance Corporation

( * ) Notice: Subject to any disclaimer, the term of this patent is extended or adjusted under 35 U.S.C. 154(b) by 0 days.

(21) Appl. No.: 13/910,929

(22) Filed: Jun. 5, 2013

(65) Prior Publication Data

US 2013/0340394 A1    Dec. 26, 2013

Related U.S. Application Data

(63) Continuation of application No. 10/685,545, filed on Oct. 14, 2003, now abandoned.

(51) Int. Cl.
*A61L 2/00* (2006.01)
*A61L 9/00* (2006.01)
*A61L 2/18* (2006.01)

(52) U.S. Cl.
USPC .............................. 422/294; 422/292; 422/28

(58) Field of Classification Search
CPC .................................................. A61L 2202/24
USPC .................................................. 422/292, 294
See application file for complete search history.

(56) References Cited

U.S. PATENT DOCUMENTS

| 2,899,799 A | 6/1959 | Korpman |
| 3,704,096 A | 11/1972 | Verses et al. |

(Continued)

FOREIGN PATENT DOCUMENTS

| EP | 0 307 173 A1 | 3/1989 |
| EP | 0 370 835 A2 | 5/1990 |

(Continued)

OTHER PUBLICATIONS

PCT International Search Report; PCT US2004/033829; Jan. 21, 2005.

(Continued)

*Primary Examiner* — Regina M Yoo

(57) ABSTRACT

There is provided an improved sterilization wrap and a method for using the improved sterilization wrap to sterilize an article. The wrap is made of at least one sheet, and preferably two sheets, of sterilization material and in some embodiments, includes an additional sheet which may be made of an absorbent material. The sheet of absorbent material may have a smaller perimeter than at least one sheet of sterilization material. One side of at least one sheet of sterilization material includes a central portion. The absorbent material may be attached to the central portion of at least one sheet of sterilization material. The article to be sterilized is placed on the sterilization wrap and is then wrapped. The absorbent material provides sterility protection for the article in addition to the at least one sheet of sterilization material and also wicks moisture away from the article after sterilization has taken place. A visual indicator may be provided to indicate whether or not the article has been exposed to adequate sterilization conditions.

19 Claims, 5 Drawing Sheets

(56) References Cited

U.S. PATENT DOCUMENTS

| | | | |
|---|---|---|---|
| 3,930,580 | A | 1/1976 | Bazeli et al. |
| 4,091,921 | A | 5/1978 | Lewis |
| 4,206,844 | A | 6/1980 | Thukamoto et al. |
| 4,342,392 | A | 8/1982 | Cox |
| 4,514,361 | A | 4/1985 | Hirsch |
| 4,579,715 | A | 4/1986 | Bruso |
| 4,596,696 | A | 6/1986 | Scoville, Jr. |
| 4,636,472 | A | 1/1987 | Bruso |
| 4,692,307 | A | 9/1987 | Bruso |
| 4,705,171 | A | 11/1987 | Eldridge |
| 4,902,478 | A | 2/1990 | Hambleton |
| 4,918,003 | A | 4/1990 | Macaro et al. |
| 5,200,147 | A | 4/1993 | Augurt |
| 5,204,062 | A | 4/1993 | Buglino et al. |
| 5,217,901 | A | 6/1993 | Dyckman |
| RE34,515 | E | 1/1994 | Foley |
| 5,435,971 | A | 7/1995 | Dyckman |
| 5,478,749 | A | 12/1995 | Dyke |
| 5,524,755 | A | 6/1996 | Deeds |
| 5,549,868 | A * | 8/1996 | Carlson, II ........................ 422/1 |
| 5,635,134 | A | 6/1997 | Bourne et al. |
| 5,942,438 | A | 8/1999 | Antonoplos et al. |
| 5,958,337 | A | 9/1999 | Bourne et al. |
| 6,051,187 | A | 4/2000 | Hughes |
| 6,217,890 | B1 * | 4/2001 | Paul et al. ..................... 424/402 |
| 6,406,764 | B2 | 6/2002 | Bayer et al. |
| 6,440,375 | B1 * | 8/2002 | Davis et al. ................... 422/300 |
| 6,517,916 | B1 | 2/2003 | Bayer et al. |
| 6,630,104 | B1 | 10/2003 | Bayer et al. |

FOREIGN PATENT DOCUMENTS

| | | |
|---|---|---|
| EP | 0 754 796 A1 | 1/1997 |
| FR | 2 521 906 | 8/1983 |
| GB | 2 360 707 | 10/2001 |
| JP | 11-34264 | 2/1999 |

OTHER PUBLICATIONS

PCT Written Opinion; PCT US2004/033829; Jan. 21, 2005.

* cited by examiner

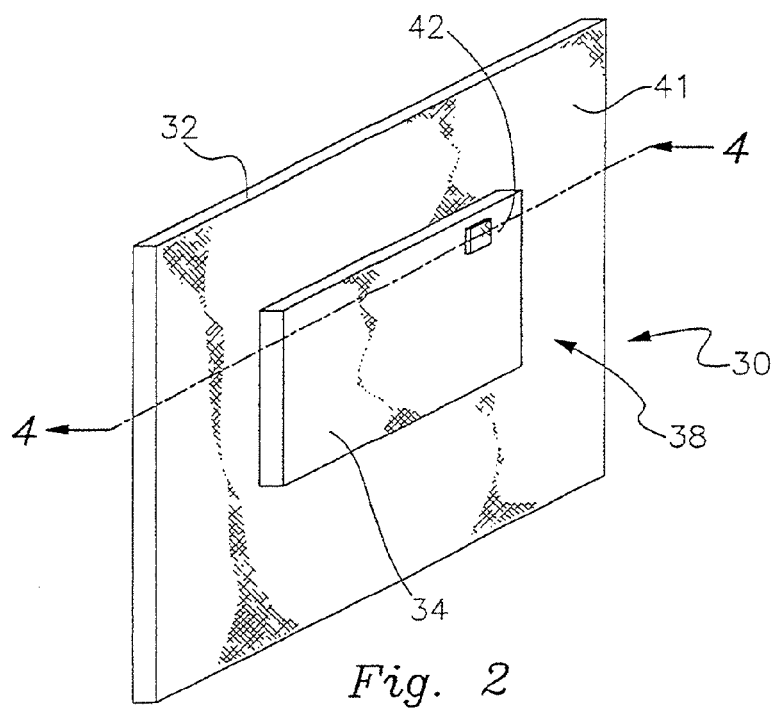
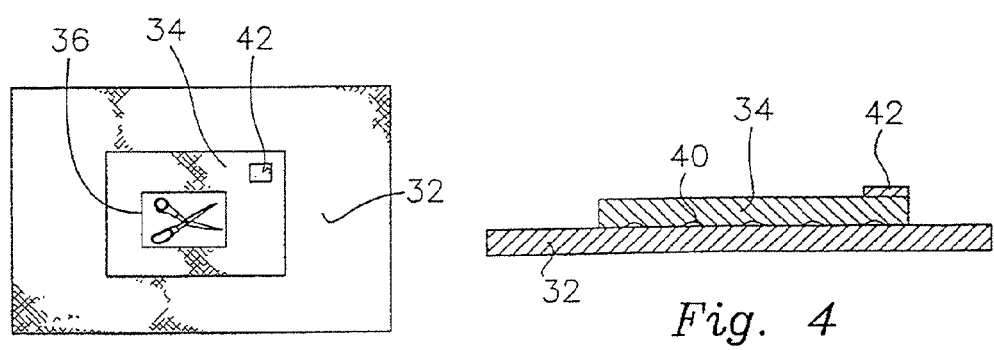

STERILIZATION WRAPS AND METHODS FOR STERILIZING ARTICLES

CROSS-REFERENCED TO RELATED APPLICATION

This application is a Continuation of U.S. application Ser. No. 10/685,545, filed Oct. 14, 2003, the disclosure of the prior application is hereby incorporated in its entirety by reference.

BACKGROUND OF THE INVENTION

This invention relates to sterilization wrap. More particularly, it relates to sterilization wrap utilizing two layers or sheets of material.

Reusable medical instruments must be sterilized prior to each use. Normally, these instruments are exposed to a sterilant to achieve sterilization. As used herein, the term sterilant is meant to refer to the sterilization effectors that are conventionally utilized with sterilization wrap, sterilization techniques, including but not limited to steam, ethylene-oxide, plasma, or the like. In order for the instruments to remain sterile after the sterilization procedure, the instruments must be wrapped in a material called sterilization wrap prior to the sterilization procedure.

The most common type of sterilization wrap is a three-ply laminate consisting of a layer of melt blown polypropylene sandwiched between two layers of spunbond polypropylene. The wrap includes bond points all across the face of the material so that the material is held together, i.e., laminated. This three-ply material is commonly referred to as "SMS", which is short for spun bond-melt blown-spun bond. Most hospitals specify SMS as the sterilization wrap to be used because SMS is sufficiently porous to permit steam, ethylene-oxide and other sterilization materials to penetrate through the material to the surgical instruments, but has filtration properties sufficient to prevent the passage of most pathogens therethrough so as to maintain sterility after the sterilization process. The wrap also protects articles during sterilization, and acts as a filtration medium for the sterilant.

In most hospitals, there is a protocol which requires surgical instruments to be wrapped with two separate sheets of material so that if one sheet becomes torn, there is a redundancy which will maintain the sterility of the surgical instruments. The wrapping of surgical instruments with two separate sheets of sterilization wrap obviously is labor intensive in that the clinician must first place the instruments on one sheet of sterilization material and wrap the instruments, and then place the wrapped package on another sheet of sterilization material and again wrap the package containing the instruments.

In an attempt to reduce the labor required to provide dual wrapping of surgical instruments, Kimberly-Clark Corporation has developed a product called "One Step® Sterilization Wrap." One Step® Sterilization Wrap is made by bonding two separate sheets of sterilization wrap together near two of the edges of the adjacent sheets. The Kimberly-Clark One Step® product is described in U.S. Pat. Nos. 5,635,134 and 5,688,476.

FIG. 1 herein shows one of the Kimberly-Clark One Step® products described in these Kimberly-Clark patents. Sterilization wrap 10 includes a top sheet 12 made of SMS and a bottom sheet 14 also made of SMS. The lengths and widths of top sheet 12 and bottom sheet 14 are identical and the outside edges of each layer align with one another. The two layers of SMS are bonded together near two opposing edges 16 and 18, as illustrated by bond lines 20 and 22. The method of bonding the two sheets together may be ultrasonic bonding. The other two opposing edges 24 and 26 are not bonded together so there is a visible gap 28 between sheets 12 and 14 so that the user of the sterilization wrap visually distinguishes the fact that there are, indeed, two sheets. Apparently the purpose for ensuring that the two sheets are visually distinguishable as separate sheets is so that the user knows with certainty that the item to be sterilized has two sheet protection. However, because of this gap 28, debris could enter the region between the two sheets. With two of the edges being unbonded, it is possible that the sheets become misaligned so that if a sharp object penetrates both sheets, the resulting holes in each sheet could also become misaligned, thus reducing ones ability to determine whether or not there is a hole through both sheets. In addition, since edges 24 and 26 are not bonded and bond lines 20 and 22 are somewhat removed from edges 16 and 18, fibers from those edges could become released from the wrap. Also, since the edges 24 and 26 are not bonded, the two sheets might be pulled apart by mistake during use. Furthermore, since the wrap shown in FIG. 1 is not sealed right to the edges 16 and 18, the user might perceive that there could be contamination between the sheets.

Recently Cardinal Health has introduced a new two sheet sterilization wrap called Simul-Wrap® which overcomes the problems of the Kimberly-Clark One Step® product described above. The Simul-Wrap® product is made of two identical sheets of SMS sterilization material which are bonded together along all four edges. The Cardinal Health Simul-Wrap® product is shown in U.S. Pat. No. 6,517,916. However, both the One Step® product and the Simul-Wrap® product have certain drawbacks. Neither product is specifically engineered to wick moisture away from the article to be sterilized after sterilization takes place. In addition, neither product provides an indication that adequate sterilization has been achieved.

OBJECTS OF THE INVENTION

It is, therefore, one object of this invention to provide an improved sterilization wrap which utilizes two layers of material.

It is another object of this invention to provide a sterilization wrap made with two layers of material which is easy to use.

It is still another object of this invention to provide a method for sterilizing an article utilizing an improved sterilization wrap.

It is further another object of this invention to provide a sterilization wrap which will wick moisture from the sterilized article.

It is yet another object of this invention to provide a sterilization wrap which is less costly to manufacture than conventional sterilization wrap.

It is another object of this invention to provide a sterilization wrap which includes a chemical visual indicator showing that the wrapped article has been exposed to adequate sterilization conditions.

It is another object of this invention to provide a two layer sterilization wrap which includes a chemical visual indicator to distinguish the sterile field from the non-sterile field when the wrap has been opened.

SUMMARY OF THE INVENTION

In accordance with one form of this invention, there is provided a sterilization wrap for wrapping an article to be sterilized. At least one sheet, and preferably two sheets, of sterilization material and a sheet of absorbent material are provided. The sheet of absorbent material is bonded to a sheet of sterilization material. The sheet of absorbent material is adapted to receive the article to be sterilized. The sheet of absorbent material (a) provides sterility protection for the article in addition to the sheet of sterilization material, and (b) wicks moisture away from the article after sterilization has taken place. The sheet of absorbent material may be made of cellulose or other absorbent matter which is capable of being formed into a sheet or layer. Preferably, the sheet of absorbent material is smaller than the sheet of sterilization material. Also, preferably, one side of the sheet of sterilization material has a central portion and the sheet of absorbent material is bonded to the central portion of the sheet of sterilization material. The sheet of sterilization material may be a different color from the sheet of absorbent material so that the user may readily differentiate between the two sheets and thus distinguish where to place the article being packaged. Also, preferably, the sheet of absorbent material is thicker or heavier than the sheet of sterilization material. In addition, a chemical visual indicator which changes color in the presence of a sterilant, such as steam, may be attached to either sheet near the article to be sterilized to indicate whether or not the article has been exposed to adequate sterilization conditions.

In accordance with another form of this invention, there is provided a sterilization wrap for wrapping an article to be sterilized. At least one sheet, and preferably two sheets, of sterilization material, and a sheet of reinforcement material are provided. The sheet of reinforcement material is bonded to a sheet of sterilization material. The sheet of reinforcement material is adapted to receive the article to be sterilized. The sheet of reinforcement material is preferably made of SMS and preferably has a higher basis weight than the sheet or either of the sheets of sterilization material.

In accordance with another form of this invention, there is provided a sterilization wrap for wrapping an article to be sterilized in which at least one sheet, and preferably two sheets bonded together at their outer peripheries, of sterilization material are provided. The first sheet has an outer periphery and a central portion. Also provided is an additional sheet of reinforcement material that is bonded to the central portion of the first sheet of sterilization material. The perimeter of the reinforcement sheet is smaller than the perimeter of the first sheet.

In accordance with another form of this invention, there is provided a sterilization wrap for wrapping an article to be sterilized, including at least one sheet of sterilization material and a sheet of absorbent material attached to the sheet of sterilization material. The sheet of absorbent material is adapted to contact the article to be sterilized. The sheet of absorbent material is also capable of wicking moisture away from the article after sterilization has taken place.

In accordance with another form of this invention, there is provided a sterilization wrap for wrapping an article to be sterilized, including at least one sheet, and preferably two sheets bonded together, of sterilization material, and a chemical visual indictor responsive to the presence of sterilant. The chemical visual indicator will indicate whether the article has been exposed to adequate sterilization conditions.

In accordance with another form of this invention, there are provided methods for sterilizing an article, including the steps of providing an article to be sterilized, and wrapping the article to be sterilized with the sterilization wraps described above, and applying sterilant to the wrapped article.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 2 is a perspective view of the sterilization wrap, in accordance with one embodiment of the subject invention;
FIG. 3 is a plan view of the sterilization wrap of FIG. 2 with an article to be sterilized received thereon;
FIG. 4 is a sectional view of the sterilization wrap of FIG. 2 taken through section line 4-4.

Figure 1:
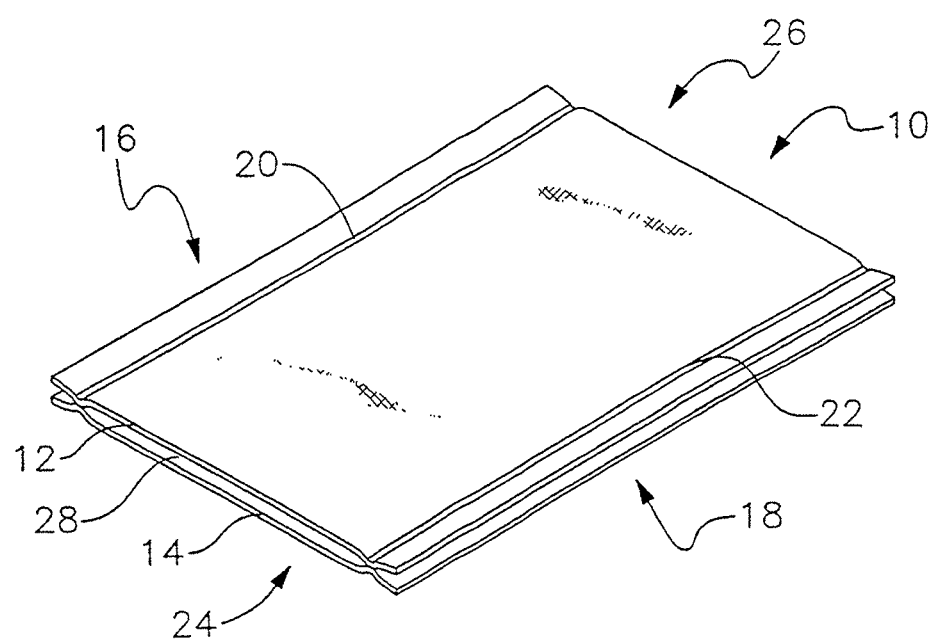
FIG. 1 is a perspective view of a prior art sterilization wrap.

The thicknesses of the materials shown in the drawings have been exaggerated for illustrative purposes and for ease of understanding.

DESCRIPTION OF THE PREFERRED EMBODIMENTS

Referring now more particularly to FIG. 2, there is provided sterilization wrap 30 having a first sheet or layer 32 and a second layer or sheet 34. Preferably, the first layer 32, which is the outside layer, is made of SMS. The first layer 32 is sometimes referred to herein as a sheet of sterilization material. The second layer 34, which is the inside layer, may be made of cellulose or some other absorbent material, which absorbs liquids and aids in drying and which also permits a sterilant, such as steam or ethylene-oxide, to pass therethrough, but inhibits pathogens from passing therethrough. Other absorbent materials could include, but are not limited to, absorbent synthetics such as hydrophillic spunmelt polyolefins, polyester, nylon, as well as polyrayons and bicomponent fibers. The second layer 34 is sometimes referred to herein as a sheet of absorbent material. In order to reduce the cost of the sterilization wrap 30 while not reducing its effectiveness, the second or inside layer 34 has a smaller perimeter than the first or outside layer 32. It is preferred that the perimeter of the inside layer 34 be at least 25% less than the outside layer 32.

As can be seen from FIG. 3, the inside layer 34 receives the article to be sterilized 36 thereon. Often the article to be sterilized is a tray containing surgical instruments. While inside layer 34 has a smaller perimeter than outside layer 32, it should be large enough so that when the article to be sterilized 36 is wrapped by sterilization wrap 30, both the bottom and sides of the article to be sterilized 36 is covered by inside layer 34.

Outside layer 32 includes a central portion 38. Inside layer 34 is adhered to the central portion 38 by means of gluing, ultrasonic bonding or some other form of adherence. Glue spots 40 are illustrated in FIG. 4. Alternatively, inside layer 34 may be made of SMS which does not have the liquid absorbent properties of cellulose. The structure of inside layer 34 when it is made of SMS is discussed below in reference to FIG. 9. In any event, this inside layer provides abuse resistance and containment properties over the prior art sterilization wrap described above.

By reinforcing the area of direct contact under the article to be sterilized 36, the primary point of potential damage to the wrap has been addressed. The method by which trays are wrapped yield several layers of material folds on the top of the article to be sterilized 36. In the event that wrapped articles get stacked on top of one another, thicker and/or heavier inside layer 34 protects the underside of the article 36 while the multiple folds are responsive to contact on the top side of article 36.

As noted, also the inner layer 34 may be made of a moisture absorbent material, such as cellulose, which provides an enhanced moisture absorption function. After the article to be sterilized 36 has been sterilized, in particularly through a steam sterilization process, moisture often remains on the article to be sterilized 36. This moisture enhances the growth of pathogens which may not have been killed during the sterilization process. By using an absorbent material, i.e., absorption material, as the material for layer 34, this moisture tends to be wicked away from the article to be sterilized 36 and more effectively dried. Thus the chances of pathogen growth on or around the article to be sterilized is greatly reduced.

It is preferred that outer layer 32 be of a different color from inner layer 34. Since inner layer 34 is always within the sterile field, this color differential will inform the sterile clinician that it is okay to touch any portion of the sterile field formed by the inside surface of outer layer 32 and inside layer 34.

it is also preferred that a sterilization chemical visual indicator 42, which may also be an integrator or emulator, be adhered to inside layer 34 or to the inside surface 41 of outside layer 32 in the vicinity of inside layer 34. The sterilization indicator could be of a chemistry which meets or exceeds the requirements of Class 1-Class 6 chemical indicators as defined by ISO-11140-1. The sterilization indicator turns color in the presence of steam or ethylene-oxide or other sterilant and will remain at that color after sterilization has taken place. This informs the clinician that the article to be sterilized has, indeed, been exposed to adequate sterilization conditions at the time that the clinician opens the wrapped article.

Sterilization indicators are known and two such indicators are described in U.S. Pat. No. 4,514,361 issued to Hirsch and U.S. Pat. No. 2,889,799 issued to Korpman, which are hereby incorporated herein by reference. Sterilization integrators are known and one such integrator is described in U.S. Pat. No. 4,448,548, which is hereby incorporated herein by reference.

The sterilization wrap described above can be manufactured using conventional equipment and techniques readily available to those skilled in the medical fabric field.

The sterilization wrap described above may be used as set forth below. The article to be sterilized 36, as shown in FIG. 3, is placed on the outside surface of inner layer 34. The article to be sterilized 36 is then wrapped utilizing standard sterilization wrapping techniques so that a portion of the inside layer 34 covers the bottom and sides of the article to be sterilized 36, and a portion of the outside layer 32 also covers the top of the article to be sterilized 36. The wrapped package is then exposed to a sterilization process. The wrapped package is subjected to sterilants, such as steam, ethylene-oxide or plasma, for a predetermined period of time so that substantially all of the pathogens which may be present on the article to be sterilized 36 are killed. The package is then stored for usage. When it is time to use the article to be sterilized 36, the package is unwrapped by the clinician. The sterile clinician will know it is all right to touch the sterile field formed by the inner layer 34 because the inner layer 34 and the outside layer 32 are different colors. The clinician will then observe the status of sterilization indicator, integrator, or emulator 42 to determine whether or not the article 36 has been exposed to adequate sterilization conditions. The article to be sterilized 36 may then be used.

The above-described improved sterilization wrap provides the two layers of protection and ease of use associated with Kimberly-Clark's One Step® and Cardinal Health's Simul-Wrap®, while having the added features of increased protection in the central area adjacent to the article to be sterilized and further providing an ability to wick moisture away from the article to be sterilized, particularly in the case of steam sterilization, and in addition, visually informs the clinician that the inside of the wrap is the sterile field and visually informs the clinician that the article has, indeed, been exposed to adequate sterilization conditions.

While FIGS. 2 through 4 show absorbent layer 34 attached to a single sheet of sterilization material, it is preferred that two (2) layers of sterilization material are utilized.

Figure 5:
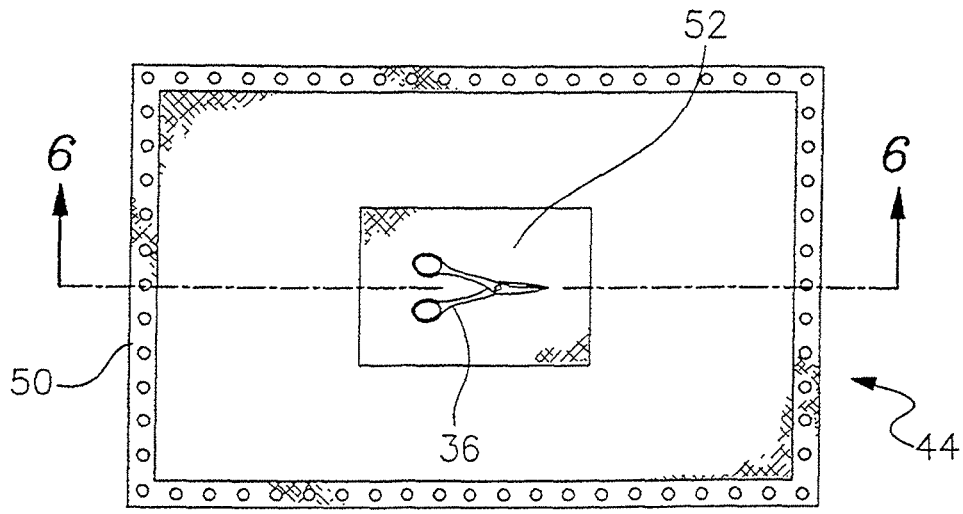
FIG. 5 is a plan view of another embodiment of the sterilization wrap in accordance with the subject invention.
Figure 6:
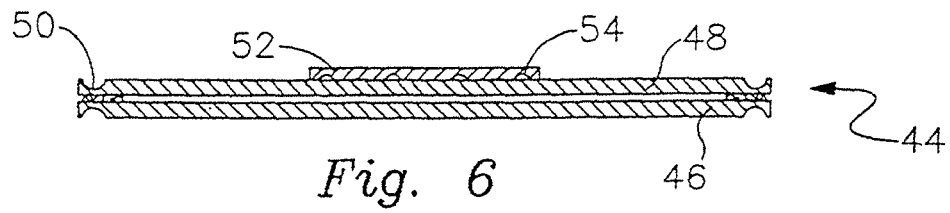
FIG. 6 is a sectional view of the sterilization wrap of FIG. 5 taken through section lines 6-6.

Referring now more particularly to FIGS. 5 and 6, two-layer sterilization wrap 44 is provided and includes outside layer 46 and inside layer 48, each made of SMS. The two layers 46 and 48 each have four edges 49, 51, 53 and 55 and are bonded together at the four edges about their outer peripheries 50, preferably by heat and pressure. The bonded two-layer sterilization material 44 may be the Simul-Wrap® product which is commercially available from Cardinal Health (1500 Waukegan Road, McGaw Park, Ill. 60085) and which is described in U.S. Pat. No. 6,517,916, the disclosure of which is hereby incorporated herein by reference. Absorbent layer 52, which may be made of cellulose or another moisture absorbing substance, is bonded to the outside of inner layer 48 by gluing or another bonding technique, as illustrated by bond sites 54. Alternatively, layer 52 may be made of SMS as discussed in reference to FIGS. 2 and 9.

Figure 7:
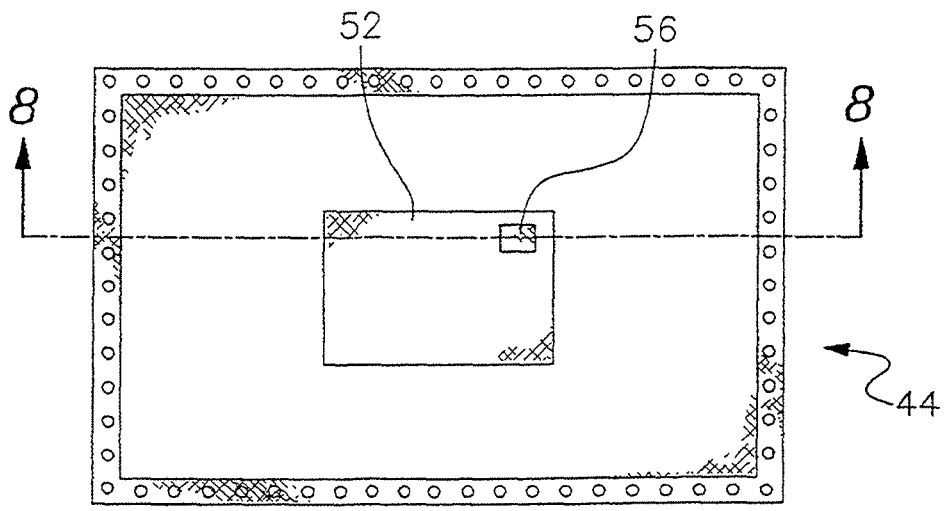
FIG. 7 is a plan view of yet another embodiment of the sterilization wrap in accordance with the subject invention.
Figure 8:
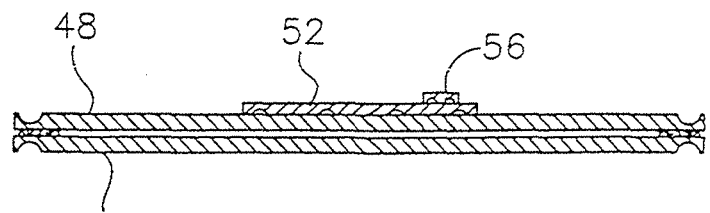
FIG. 8 is a sectional view of the sterilization wrap of FIG. 7 taken through section lines 8-8.

Referring now more particularly to FIGS. 7 and 8, a sterilization indicator device 56 is attached to absorbent layer 52.

Figure 9:
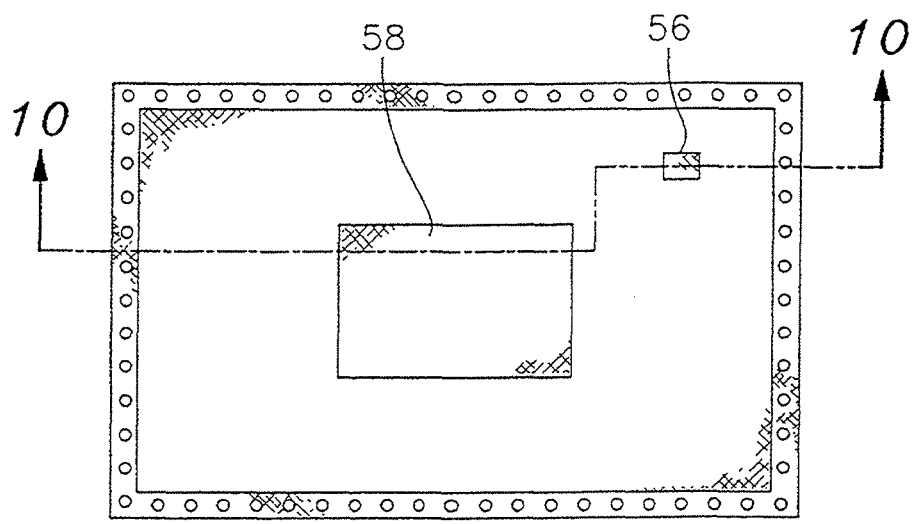
FIG. 9 is a plan view of yet another embodiment of the sterilization wrap in accordance with the subject invention.
Figure 10:
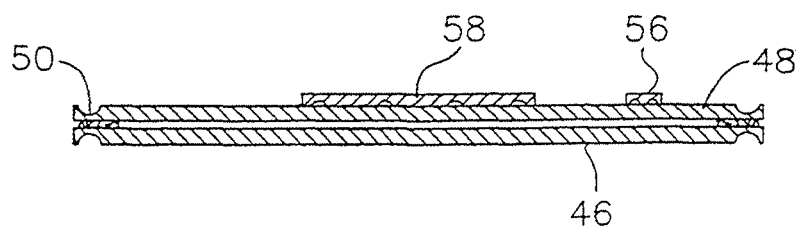
FIG. 10 is a sectional view of the sterilization wrap of FIG. 9 taken through section lines 10-10.

Referring now more particularly to FIGS. 9 and 10, the absorbent layer 52 has been replaced with a reinforcement panel 58 made of SMS. Panel 58 has an equal to or higher basis weight than either layer 46 or 48. The basis weight of panel 58 may range from 1.0 ounces per square yard (osy) to 3.0 osy. The basis weight for each of layers 46 and 48 may range from 0.75 osy to 2.9 osy. While reinforcement panel 58 does not provide the moisture wicking function of absorption layer 52, it provides additional protection for the article to be sterilized 36 as shown in FIG. 5, which is to be placed on reinforcement panel 58. The embodiment shown in FIGS. 9 and 10 results in a more cost effective product than the use of two full sheets of SMS, but is equal functionally, since less material is used. FIG. 9 also shows a sterilization indicator 56 having been placed on the outside surface of inner panel 48.

Figure 11:
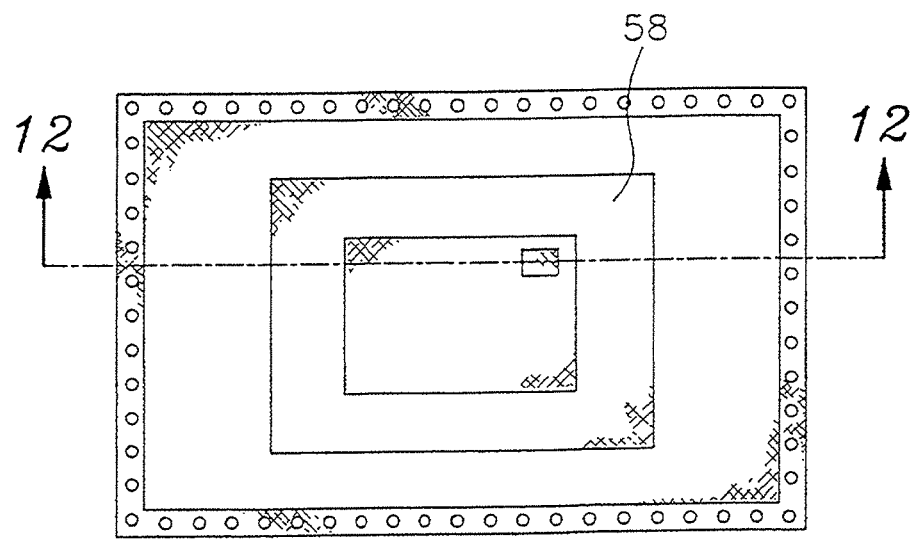
FIG. 11 is a plan view of yet another embodiment of the sterilization wrap in accordance with the subject invention.
Figure 12:
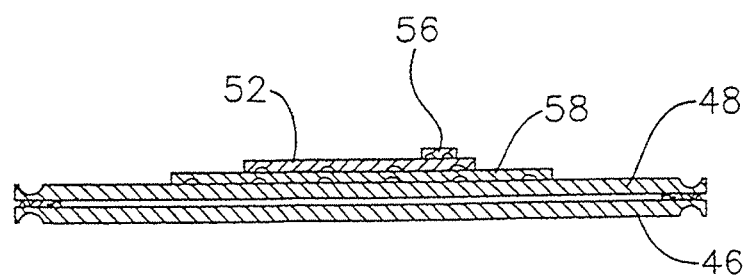
FIG. 12 is a sectional view of the sterilization wrap of FIG. 11 taken through section lines 12-12.

The embodiment of FIGS. 11 and 12 represents a combination of the embodiments of FIGS. 7 and 9. That is, reinforcement panel 58 is attached to inside SMS layer 48. Absorbent layer 52 is, in turn, attached to reinforcement layer 58. Chemical visual indicator 56 is attached to absorbent layer 52. Alternatively, indicator 56 may be attached to reinforcement layer 58 or to inside layer 48. In addition, in the embodiment of FIGS. 11 and 12, outside SMS layer could be eliminated.

From the foregoing description of the preferred embodiments of the invention, it is apparent that many modifications may be made therein. It should be understood, however, that these embodiments of the invention are exemplifications of the invention only and that the invention is not limited thereto. It is to be understood, therefore, that it is intended in the appended claims to cover all modifications as fall within the true spirit and scope of the invention.

What is claimed is:

1. A sterilization wrap for wrapping an article to be sterilized comprising:
a first sheet of sterilization material, the first sheet having an outer periphery and a central portion, wherein the first sheet is made of spunbonded-meltblown-spunbonded material (SMS);
a sheet of reinforcement material that is bonded to the central portion of the first sheet and adapted to receive the article to be sterilized, wherein the perimeter of the sheet of reinforcement material is smaller than the perimeter of the first sheet, wherein the sheet of reinforcement material is made of spunbonded-meltblown-spunbonded material (SMS) of equal or higher basis weight than the SMS of the first sheet, and wherein the sheet of reinforcement material has a different color than the first sheet; and
a second sheet of sterilization material made of SMS and bonded to outer periphery of the first sheet;
wherein the sterilization wrap is configured such that when the article to be sterilized is wrapped by the sterilization wrap, both the bottom and the sides of the article to be sterilized is covered by the sheet of reinforcement material and the top of the article to be sterilized is covered by the first sheet.

2. The sterilization wrap as set forth in claim 1, wherein each of said first and second sheets of sterilization material includes four edges about their peripheries; said four edges of said first sheet of sterilization material being bonded to said four edges of said second sheet of sterilization material.

3. The sterilization wrap as set forth in claim 1, wherein the perimeter of said sheet of reinforcement material is at least 25% less than the perimeter of said first sheet of sterilization material.

4. The sterilization wrap as set forth in claim 1, wherein said first sheet of sterilization material has two sides; one side of said two sides of said first sheet of sterilization material having a central portion; said sheet of reinforcement material bonded to said first sheet of sterilization material at said central portion of said one side.

5. The sterilization wrap as set forth in claim 1, wherein said sheet of reinforcement material is bonded to said first sheet of sterilization material by glue.

6. The sterilization wrap as set forth in claim 1, wherein said sheet of reinforcement material is bonded to said first sheet of sterilization material by heat and pressure.

7. The sterilization wrap as set forth in claim 1, further including a chemical visual indicator; said chemical visual indicator being in one visual state prior to exposure to sterilant and being in another visual state after exposure to sterilant; said chemical visual indicator being attached to said sterilization wrap so as to indicate whether or not the article to be sterilized has been exposed to adequate sterilization conditions.

8. The sterilization wrap as set forth in claim 7, wherein said chemical visual indicator is attached to said first sheet of sterilization material.

9. The sterilization wrap as set forth in claim 7, wherein said chemical visual indicator changes color after having been exposed to steam.

10. The sterilization wrap as set forth in claim 7, wherein said chemical visual indicator meets the requirements of ISO 11140-1.

11. A method for sterilizing art article comprising the steps of:
providing an article to be sterilized;
providing a sterilization wrap which comprises:
a first sheet of sterilization material, the first sheet having an outer periphery and a central portion, wherein the first sheet is made of spunbonded-meltblown-spunbonded material (SMS);
a sheet of reinforcement material that is bonded to the central portion of the first sheet and adapted to receive the article to be sterilized, wherein the perimeter of the sheet of reinforcement material is smaller than the perimeter of the first sheet, wherein the sheet of reinforcement material is made of spunbonded-meltblown-spunbonded material (SMS) of equal or higher basis weight than the SMS of the first sheet, and wherein the sheet of reinforcement material has a different color than the first sheet; and
a second sheet of sterilization material made of SMS and bonded to outer periphery of the first sheet;
wrapping the article to be sterilized with the sterilization wrap such that both the bottom and the sides of the article to be sterilized is covered by the sheet of reinforcement material and the top of the article to be sterilized is covered by the first sheet; and
applying sterilant to the wrapped article.

12. The method for sterilizing an article as set forth in claim 11, wherein each of said first and second sheets of sterilization material includes four edges about their peripheries; said four edges of said first sheet of sterilization material being bonded to said four edges of said second sheet of sterilization material.

13. The method as set forth in claim 11, wherein the perimeter of said sheet of reinforcement material is at least 25% less than the perimeter of said first sheet of sterilization material.

14. The method as set forth in claim 11, wherein said first sheet of sterilization material has two sides; one side of said two sides of said first sheet of sterilization material having a central portion; said sheet of reinforcement material bonded to said first sheet of sterilization material at said central portion of said one side.

15. The method as set forth in claim 11, wherein said sheet of reinforcement material is bonded to said first sheet of sterilization material by heat and pressure.

16. The method as set forth in claim 11, wherein the sterilization wrap further includes a chemical visual indicator; said chemical visual ndicator being in one visual state prior to exposure to sterilant and being in another visual state after exposure to sterilant; said chemical visual indicator being attached to said sterilization wrap so as to indicate whether or not the article to be sterilized has been exposed to adequate sterilization conditions.

17. The method as set forth in claim 16, wherein said chemical visual indicator is attached to said sheet of first sheet of sterilization material.

18. The method as set forth in claim 16, wherein said chemical visual indicator changes color after having been exposed to steam.

19. The method as set forth in claim 16, wherein said chemical visual indicator meets the requirements of ISO 11140-1.

* * * * *

UNITED STATES PATENT AND TRADEMARK OFFICE
CERTIFICATE OF CORRECTION

PATENT NO. : 8,821,808 B2  
APPLICATION NO. : 13/910929  
DATED : September 2, 2014  
INVENTOR(S) : Cannady et al.

Page 1 of 1

It is certified that error appears in the above-identified patent and that said Letters Patent is hereby corrected as shown below:

IN THE CLAIMS

In claim 11, column 8, line 4, "art" should read --an--.

In claim 16, column 8, line 50, "ndicator" should read --indicator--.

Signed and Sealed this  
Ninth Day of June, 2015

Michelle K. Lee  
*Director of the United States Patent and Trademark Office*